United States Patent
Laukenmann et al.

(10) Patent No.: US 6,640,842 B1
(45) Date of Patent: Nov. 4, 2003

(54) METHOD AND DEVICE FOR FILLING NEEDLE-FREE INJECTORS

(75) Inventors: Bernd Laukenmann, Crailsheim (DE); Michael Nikolaus Mueller, Westernach (DE); Juergen Rothbauer, Michelfeld (DE); Georg Alfred Kallmeyer, Mannheim (DE); Theo Wilfried Arnitz, Ettlingen (DE)

(73) Assignee: Inova Pharma Systems GmbH, Schwaebisch Hall (DE)

(*) Notice: Subject to any disclaimer, the term of this patent is extended or adjusted under 35 U.S.C. 154(b) by 0 days.

(21) Appl. No.: 10/031,262

(22) PCT Filed: Apr. 20, 2000

(86) PCT No.: PCT/EP00/03642
§ 371 (c)(1),
(2), (4) Date: May 10, 2002

(87) PCT Pub. No.: WO00/64744
PCT Pub. Date: Nov. 2, 2000

(30) Foreign Application Priority Data
Apr. 20, 1999 (DE) .......................... 199 18 721

(51) Int. Cl.$^7$ .............................. B65B 1/04; B65B 3/04
(52) U.S. Cl. .............................. 141/2; 141/18; 141/21; 141/27; 604/416
(58) Field of Search .......................... 141/2, 4, 18–26, 141/27; 604/403–416

(56) References Cited

U.S. PATENT DOCUMENTS

| 4,010,747 A | * | 3/1977 | Clark et al. ................ 604/500 |
| 4,338,980 A | | 7/1982 | Schwebel et al. |
| 4,713,925 A | | 12/1987 | Kafkis |

FOREIGN PATENT DOCUMENTS

| DE | 43 20 098 A1 | 12/1994 |
| DE | 199 18 721.5 | 4/2000 |
| FR | 2 668 118 A1 | 4/1992 |
| WO | WO 96/13289 | 5/1996 |
| WO | WO 97/22375 | 6/1997 |
| WO | WO 97/36785 | 10/1997 |

* cited by examiner

Primary Examiner—Steven O. Douglas
(74) Attorney, Agent, or Firm—Quarles & Brady LLP (57) ABSTRACT

In a method and a device for filling needle-free injectors, it is proposed that filling takes place through the injector discharge opening and where the piston stopper has been previously inserted. Filling takes place in such a way that, independently of tolerances of the injector, the interior space is filled to the brim in an at least approximately bubble-free manner. It is not absolutely necessary to measure or dose the liquid to be filled. The filled state is either established through the disappearance of the vacuum in the interior space, or through the piston having reached a specific position during displacement.

11 Claims, 6 Drawing Sheets

METHOD AND DEVICE FOR FILLING NEEDLE-FREE INJECTORS

BACKGROUND OF THE INVENTION

Needle-free injectors, capsules and the like are generally filled from the side from which the piston stopper is inserted. However, there are also cases where filling takes place from the side of the discharge opening, i.e. through the latter. Hereinafter for such containers only the expression injectors is used, but this term also covers other containers.

The problem of the invention is to provide a method and a device for the exact filling of different containers. It must be possible to fill the container up to the brim and at least in an approximately bubble-free manner.

SUMMARY OF THE INVENTION

According to the invention, a piston stopper is inserted in an injector, an interior space of the injector is evacuated, and a liquid is then used to A fill the evacuated space. The method is usable with injectors of different sizes without conversion being necessary.

According to the invention the filling of the injector housing can take place by so-called suction filling at atmospheric pressure or under a slight vacuum of the liquid.

According to the invention, prior to the start of evacuation, the piston stopper can be brought to a position corresponding to the desired filling volume. The piston stopper is retained in this position during evacuation and filling. If use is made of a tight fitting piston, no further measures are required for maintaining the piston in this position. The position can be determined by a stop.

According to the invention for determining the state when the interior space of the injector is completely filled, use can be made of the disappearance of the vacuum.

Alternatively for filling the evacuated injector housing it is also possible to fill the injector in such a way that firstly the piston stopper is inserted and then liquid is filled through the discharge opening until the injector is completely filled.

According to the invention the piston stopper can be displaced by the pressure of the filled liquid until the injector filling volume is reached.

According to the invention for this purpose the filling volume can be preset by means of a dosing system, e.g. suitable pumps.

It is also possible and is proposed by the invention that the piston is moved by the pressure of the filled liquid until a desired position is reached and the reaching of said desired position is used for detecting the filled state. Also in this manner of filling the interior space of the injector is filled to the brim in bubble-free manner. The desired position can e.g. be determined by a fixed stop. In order to be able to carry out filling sufficiently rapidly in this case, it is possible for filling to take place with a much higher overpressure by so-called pressure filling.

The reaching of the stop can be used for ending the filling process.

If in the filled state of the injector there is still an overpressure in the liquid, it can be removed by suitable measures, e.g. by a bypass in the liquid feed line.

In the case of pressure filling it is not absolutely necessary for there to be a prior evacuation of the injector to be filled and in this case there is no need for the vacuum bell jar.

The discharge opening can be closed by a stopper after filling the injector.

The device proposed by the invention can have a mounting support for the injector to be filled and the mounting support can preferably have a stop for the piston stopper.

According to the invention it is also possible for a bell jar to be retained on the filling needle in such a way that it can still be moved relative to the filling needle, preferably against the action of a spring. It is possible in this way to use the filling needle drive for lowering the bell jar.

According to the invention the closing device can have a closing rod axially traversing the filling needle and which can be moved by a drive. Such a filling needle has the advantage that it closes without drops being formed. Through a corresponding choice of material and an easily dismantlable construction with few dead spaces, it is easy to clean and sterilize the filling needle.

The bell jar can have a suction opening surrounding the filling needle, so that evacuation and filling are integrated into a common filling member.

When dimensioning the system account must be taken of pharmaceutical standpoints. Sterile filters can be located at all product-contacting inlets and outlets for the system.

BRIEF DESCRIPTION OF THE DRAWINGS

Further features, details and advantages of the invention can be gathered from the following description and the attached drawings, wherein show.

Figure 1:
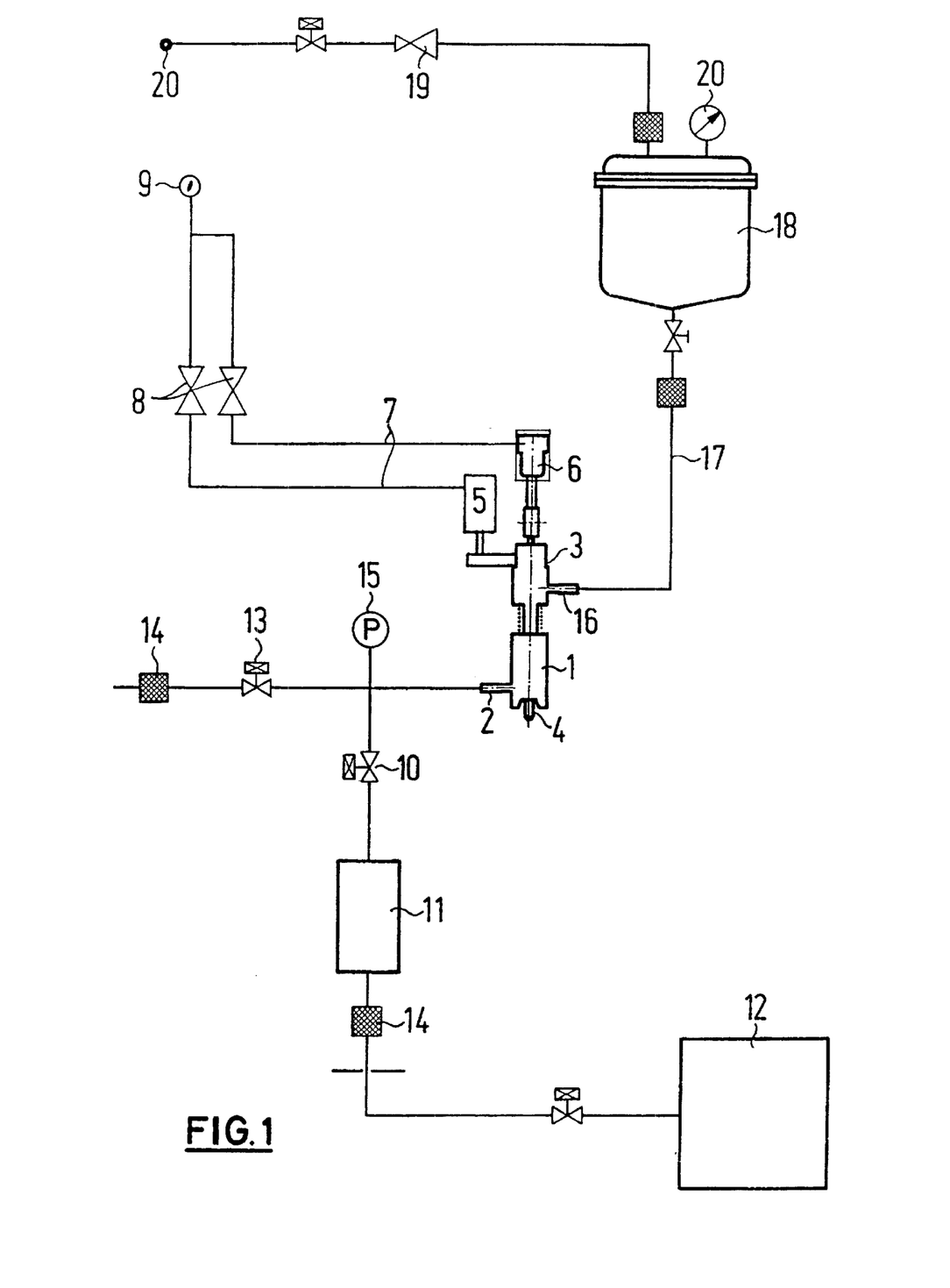
FIG. 1 Diagrammatically the arrangement of a suction filling device according to the invention.

FIG. 1 provides an overall view of a suction filling system in which is provided a device according to the invention and which is shown in the centre of FIG. 1. It contains a vacuum bell jar 1, which is provided with a vacuum connection 2. The device also contains a filling device 3 containing a filling needle 4. The filling needle 4 projects from the bell jar 1 at the underside thereof. The injector to be filled and which is not shown in FIG. 1 is placed directly below the bell jar 1 and the filling needle 4. The filling needle 4 and bell jar 1 can be together lowered and then raised again by a first drive 5, which can e.g. be controlled by compressed air. With the aid of a second coaxial drive 6 it is possible for a closing device to open and close the filling needle 4. For controlling these two drives pressure lines 7 are provided, which are connected by means of control valves 8 with a compressed air source 9.

The vacuum connection 2 is connected by means of a valve 10 to a vacuum tank 11, where the vacuum is maintained by a vacuum pump 12. The connection 2 can be vented by a further valve 13. All the lines contain sterile filters 14, because the liquid to be filled is generally constituted by a medical liquid. The pressure prevailing in the line leading to the connection 2 can be measured with the aid of a measuring device 15.

The filling needle 4 has a connection 16 for the liquid to be filled. Said connection 16 is connected by means of a line 17 to a tank 18 housing the liquid to be filled. For producing a pressure for delivering the liquid, a connection to a compressed air source 20 can be made by means of a regulating valve 19. The pressure prevailing in the tank 18 can also be measured with the aid of a measuring device 20.

The different valves can be opened and closed by means of a corresponding, not shown control system.

Figure 1A:
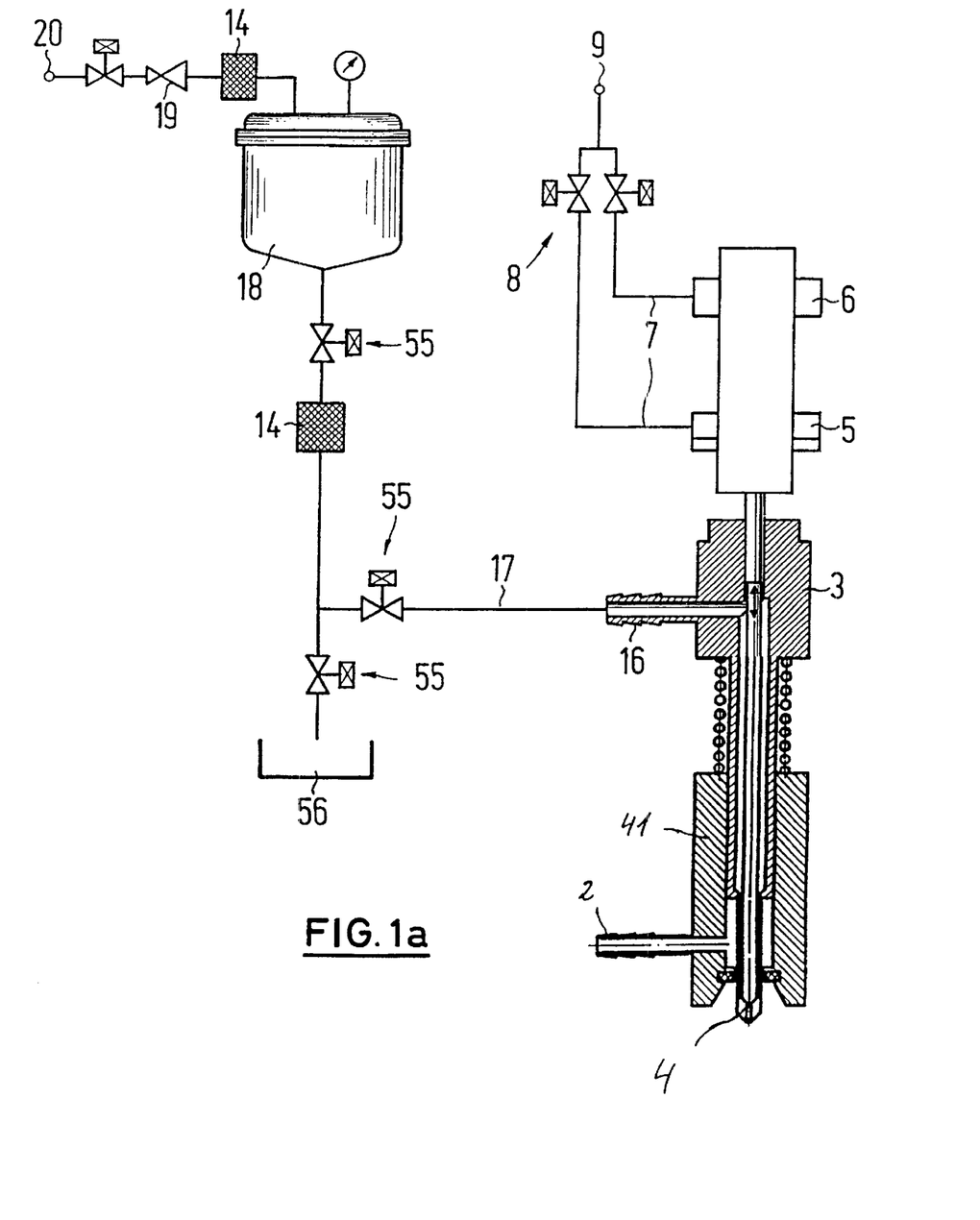
FIG. 1a Diagrammatically the arrangement of a pressure filling device according to the invention.

FIG. 1a diagrammatically shows the arrangement of a pressure filling device according to the invention. The device contains a filling device 3 with its filling needle 4. The filling needle 4 projects at the underside from the filling device 3 in the direction of the injector to be filled and which is not shown in FIG. 1a. The filling device 3 with its filling needle 4 can be lowered and raised again by the first drive 5, which can, as shown, e.g. be controlled by compressed air. The bell jar 1 comes into sealing engagement with the sealing sleeve 44 and then the injector and the space in the sealing sleeve 44 can be evacuated. By means of a second, coaxial drive 6 a closing device can open and close the filling needle 4. For controlling said two drives pressure lines 7 are provided, which are connected by control valves 8 to a compressed air source 9.

The filling needle 4 has a connection 16 for the liquid to be filled. Said connection 16 is connected by means of the line 17 to the pressure tank 18, which houses the liquid to be filled. For producing an adequate filling pressure, i.e. an overpressure in the pressure tank 18, a connection to a compressed air source 20 can be provided by means of a regulating valve 19. To prevent contamination of the liquid, which can in particular be a medical liquid, by means of the supplied compressed air, a sterile filter 14 is preferably located on the compressed air supply side between the regulating valve 19 and the pressure tank 18. In addition, e.g. electrically operable control valves 55 are located in the line 17. In the fluid path between the tank 18 and filling needle 4 in line 17 can be provided a further sterile filter 14. There is also a liquid path leading from the line 17 to a liquid collecting vessel 56 and by means of which the line 17 can be pressure-relieved.

Figures 2, 3:
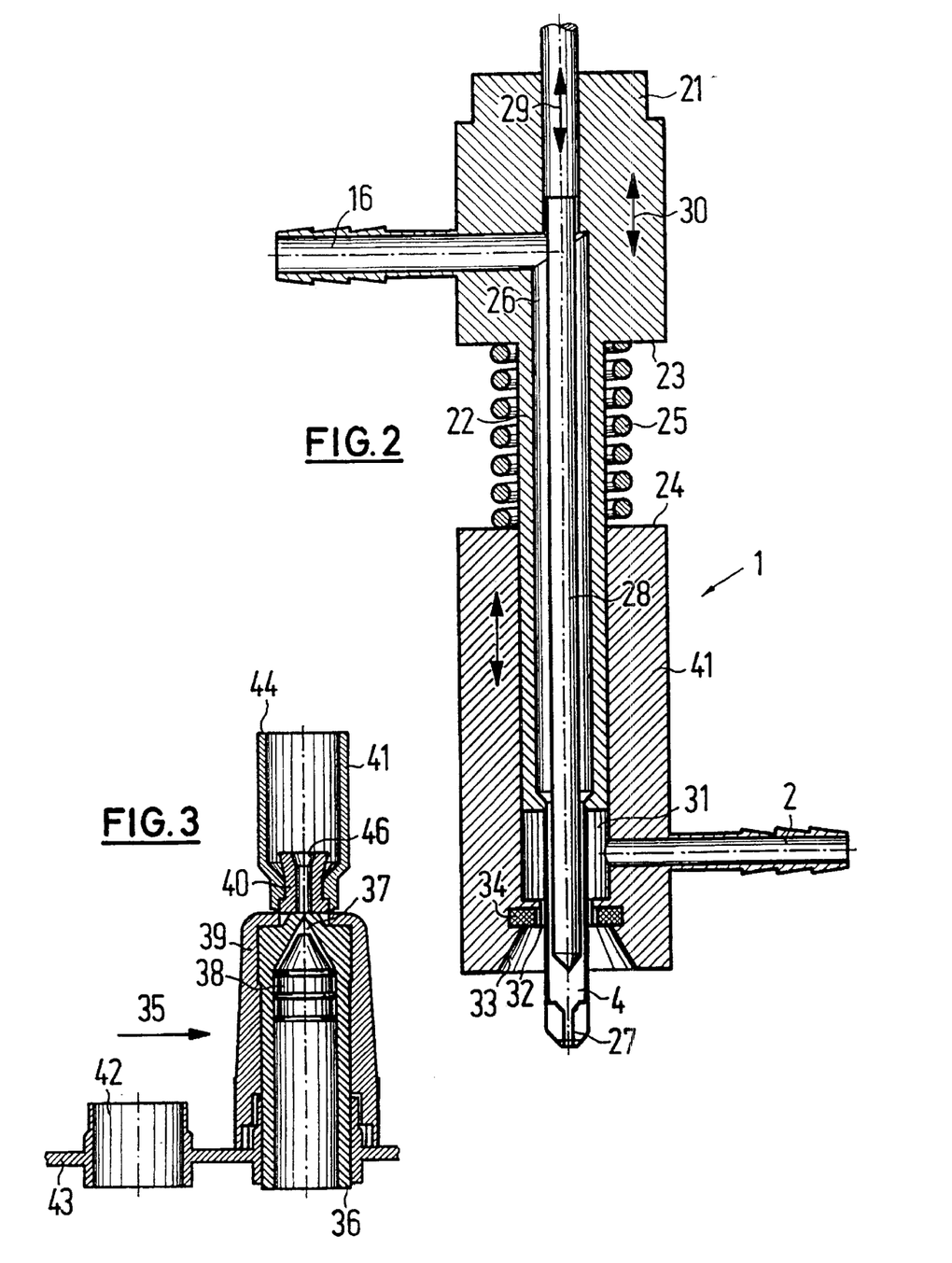
FIG. 2 Part of the device according to FIG. 1, namely a bell jar and a filling needle.
FIG. 3 A mounting support for an injector to be filled.

FIG. 2 shows on a larger scale details of the vacuum bell jar 1 and filling needle 4. A hollow, cylindrical attachment 22, on whose cylindrical outside is displaceably guided the bell jar 1, is fitted to a component 21 into which issues the connection 16 for the liquid to be filled. Between a shoulder 23 of component 21 and an end face 24, facing the same, of the bell jar 1 extends a spring 25. Through said hollow cylindrical attachment 22 extends a pipe 26, which in the vicinity of its free end passes into the filling needle 4. In the vicinity of its free end and at the bottom in FIG. 2, the filling needle 4 has an opening with a much smaller diameter than its external diameter. The pipe 26 is connected to the connection 16.

Through the pipe 26 and filling needle 4 extends a closing rod 28, which passes through a lateral opening in the vicinity of the upper end of the pipe 26 through the wall of the feed line for the liquid, where a not shown sealing takes place. The rod is connected to the aforementioned drive 6, shown in FIG. 1, and can be moved in the direction of the double arrow 29.

The drive 5 can move the component 21 and therefore the filling needle 4 in the direction of the double arrow 30. During the downward movement of the component 21 and consequently the filling needle 4, simultaneously the bell jar 1 is moved. Only when the bell jar 1 strikes against a body, does it stop, whereas the filling needle 4 can be moved on.

The vacuum connection 2 issues into an interior space 31 surrounding the filling needle and from which air can be sucked through a narrow, annular clearance 32 from the area surrounding the filling needle and from outside the bell jar. The bell jar 1 has a frustum surface 33 surrounding said clearance 32 and on whose end facing the clearance 32 is provided a seal 34.

Figures 2A, 3A:
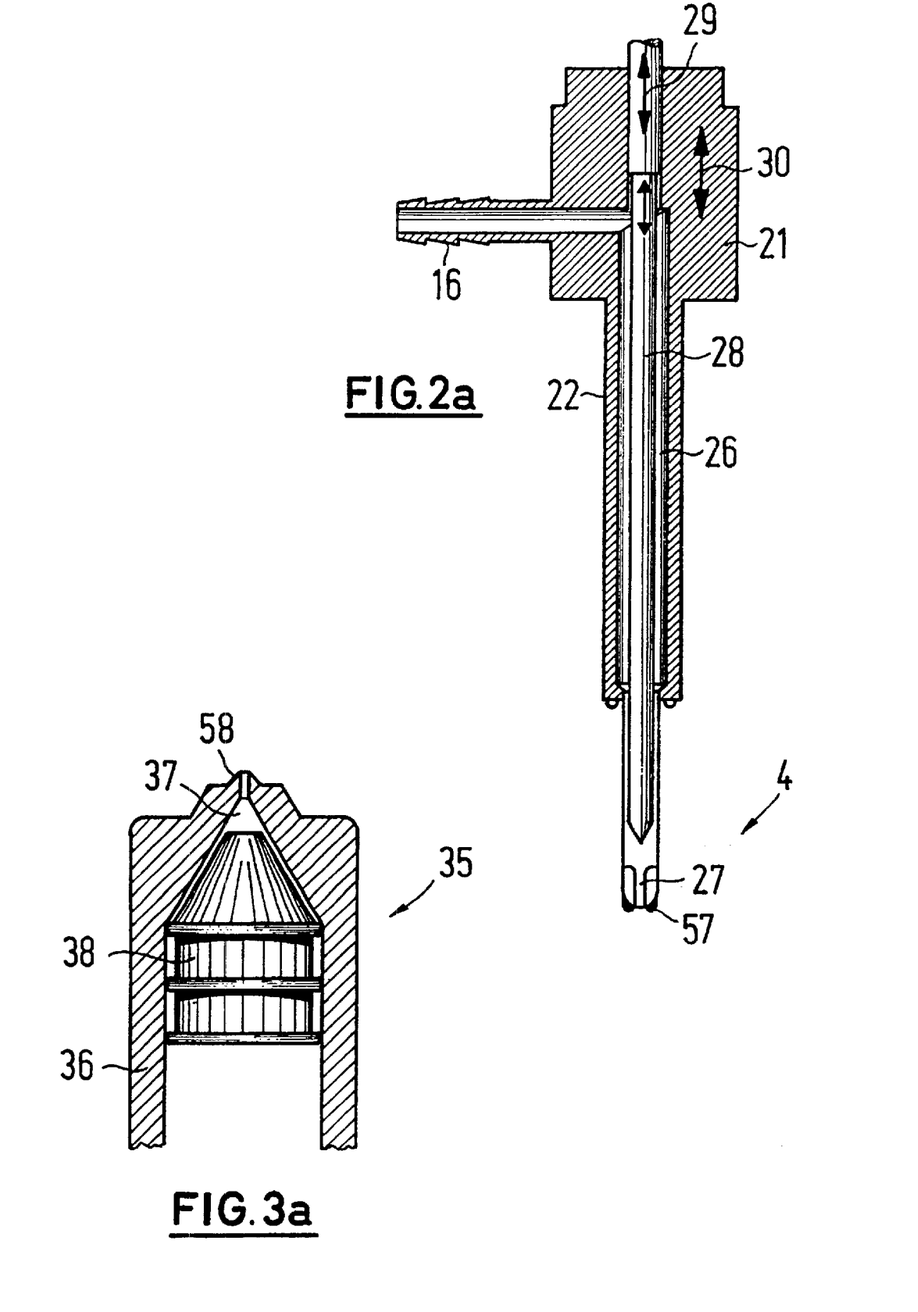
FIG. 2a Part of the device according to FIG. 1a, namely a filling needle.
FIG. 3a The arrangement of the stopper in the injector prior to filling.

FIG. 2a diagrammatically shows the filling needle 4 for filling injectors having no sealing system for sealing the injector-needle tip interface. The bell jar 1 is not shown. At its leading edge which comes into engagement with the injector, the filling needle has a seal 57 so as to permit a pressure-tight engagement on the injector. The connection 16 for the filling device 3 issues into the component 21. From the component 21 a hollow, cylindrical attachment 22 projects in the direction of the injector. Through the hollow cylindrical attachment 22 extends a pipe 26, which in the vicinity of its free end passes into the filling needle 4. In the vicinity of its free end, at the bottom in FIG. 2a, the filling needle 4 has an opening 27 with a diameter much smaller than its external diameter.

A fluid connection exists between the pipe 26 and the connection 16. Through the pipe 26 and the filling needle 4 extends a closing rod 28, which passes through a lateral opening in the vicinity of the upper end of the pipe 26 through the wall of the liquid feed line. The passage point of the closing rod 28 through the pipe 26 has a pressure-tight construction, so that no liquid leaks can occur. This seal is not shown. The closing rod 28 is connected to the drive 6 shown in FIG. 1 and can be moved in the direction of the double arrow 29.

The drive 5 can move the component 21 and therefore the filling needle 4 in the direction of the double arrow 30, i.e. towards or away from the injector. During the downward movement of component 21 the filling needle 4 is moved in the direction of the injector until the seal 57 sealingly engages on said injector.

The devices shown in FIGS. 2 and 1a cooperate with the injector 35 shown in FIG. 3. The injector contains a glass body 36, which is intended for receiving the liquid and which has a cylindrical interior space 37. In said interior space is located a piston stopper 38, which has three circumferential seals and as a result is held in the interior space. On the top side in FIG. 3 the cylindrical interior space 37 passes into a conical space, which leads to the outside via a relatively small discharge opening.

The glass body 36 with the piston stopper 38 is inserted in an external plastic sleeve 39, which forms a mounting support for a sealing sleeve 40 leading to the discharge opening. On the side remote from the glass body 36 the plastic sleeve 39 passes into a further sleeve 41 having a somewhat smaller external diameter.

The injector 35 engages in a sleeve 42 of a reception means 43 used for transporting and retaining the injectors 35. The reception means has a plate-like construction and serves to receive several injectors 35.

The terminal edge 44 of the sleeve 41 remote from the glass body 36 is dimensioned in such a way that it is intended and suitable for engagement on the underside of the seal 34 of the bell jar 1. For filling purposes the bell jar 1 is lowered onto the sleeve 41 until its terminal edge 44 engages against the seal 34. Through the sealing sleeve 40 there is an evacuation of the interior space of the glass body 36 between its discharge opening and the piston stopper 38. The filling needle 4 can then be moved until it comes into contact with the sealing sleeve 40 through which the filling of the glass body 36 also takes place.

FIG. 3a shows in the form of a larger scale detail the design of an injector, which is more particularly suitable for use in the case of pressure filling. In FIG. 3a is shown the glass body 36 in which the piston stopper 38 is displaceably mounted. Closed by the piston stopper 38, the cylindrical interior space 37 is formed inside the glass body. For the fluid-tight engagement of the filling needle-side seal 57 the glass body 36 has a conical protuberance 58, which is particularly advantageous for pressure fillings.

The procedural sequence is illustrated and described relative to FIGS. 4 to 9 showing the different stages of the method proposed by the invention.

Figure 4:
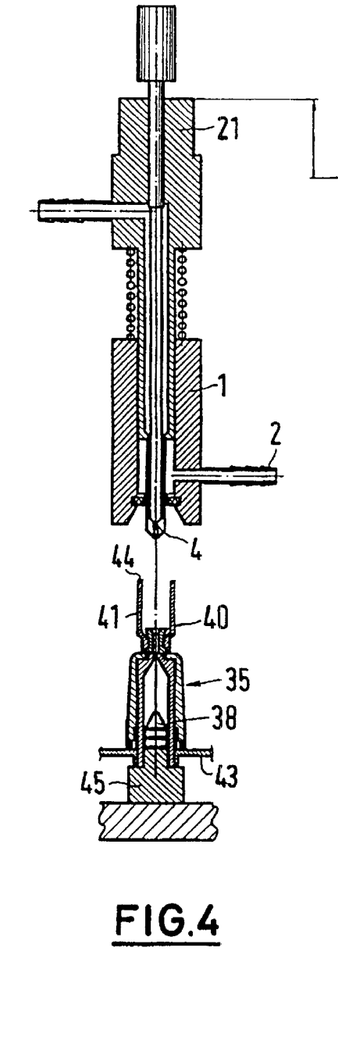
FIGS. 4 to 9 The different stages of the device during injector filling.
Figures 5, 6:
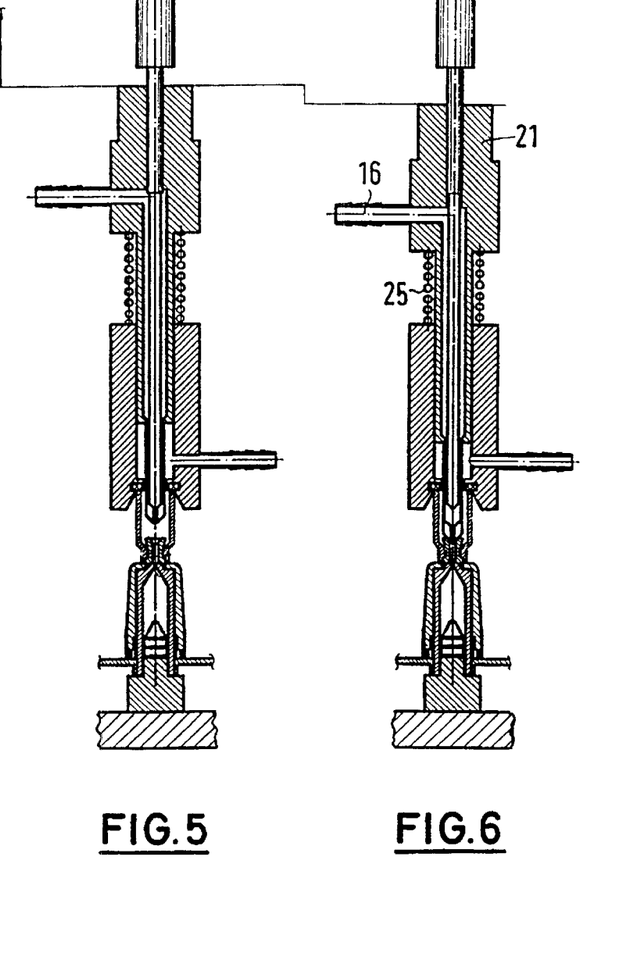

FIG. 4 shows the starting position for a possible method sequence the injector 35 is retained in the reception means 43. It is mounted on a stop 45 in such a way that the piston stopper 38 assumes a specific position, which corresponds to the desired position of the piston stopper 38. The discharge opening and sealing sleeve 40 are axially aligned with respect to the filling needle 4. By operating the drive 5 the component 21 with the filling needle 4 and vacuum bell jar 1 are lowered. This movement is continued until the seal 34 rests on the terminal edge 44 in such a way that the spring is pretensioned and as a result height differences between the capsules are compensated, as shown in FIG. 5. The connection 2 is now placed under a vacuum, so that the air is sucked out of the interior space 37 above the piston stopper 38 through the annular clearance 32. The sealed interior space of the sleeve 41 and the interior of the glass body 36 are evacuated. As soon as evacuation is ended, i.e. the vacuum reaches a sufficiently high value, the component 21 is lowered further, so that the spring 25 is further tensioned and the filling needle 4 is brought into contact with the outer opening 46 of the sealing sleeve 40, as shown in FIG. 6. By operating the drive 6 the closing rod 28 is now raised, so that the opening 27 of the filling needle 4 is opened, as shown in FIG. 6. The liquid can now flow through the connection 16 and filling needle 4 into the evacuated interior space 37 of the glass body 36. As soon as the vacuum in the interior space is eliminated, said space is filled.

Figures 7, 8, 9:
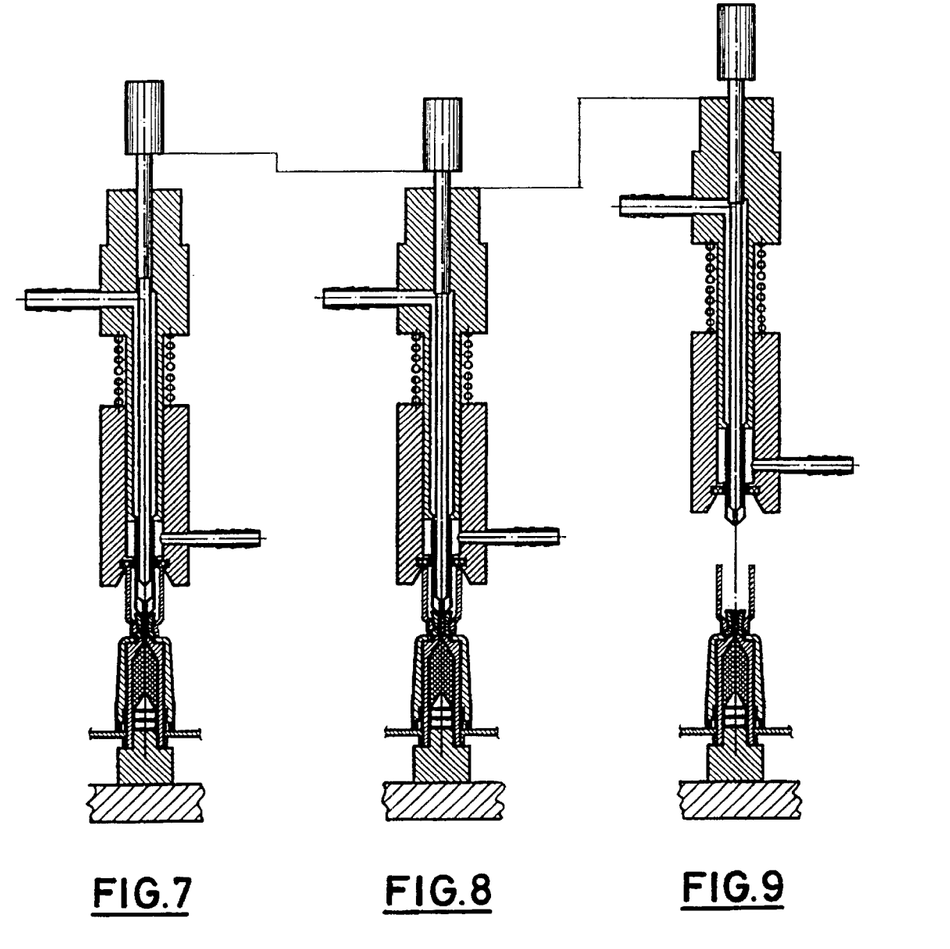

As soon as the interior space 37 is filled, cf. FIG. 7, a bypass is opened in order to reduce any vacuum present. The closing rod 28 is lowered again until it closes the opening 27, as shown in FIG. 8. At the latest at this time, the space bounded by the sleeve 41 is again vented via the bell jar 1, so that the bell jar 1 can again be raised from the injector 35. The unit constituted by the bell jar 1, component 21 and filling needle 4 is then raised, so that the filled injector 35 can be transferred.

In the method described with reference to FIGS. 4 to 9 the piston stopper 38 was located in its final desired position prior to the commencement of evacuation and filling.

The method can also be such that the piston stopper is moved further into the interior space prior to the start of evacuation. Such a starting position is shown in FIG. 3. It is appropriate in this case to carry out filling under a higher pressure in order to move the piston stopper 38 to the outside until it e.g. engages on the stop 45. Here again the injector 35 is filled to the brim and at least approximately in bubble-free manner.

What is claimed is:

1. Method for filling needle-type injectors (35), wherein
    a piston stopper (38) is inserted in the injector (35), the interior space (37) of the injector (35) is evacuated from the side of the discharge opening,
    a liquid is filled through the discharge opening and wherein filling is ended when the interior space (37) of the injector (35) is completely filled, and
    prior to the start of the evacuation, the piston stopper (38) is placed at a position corresponding to the desired filling volume and
    said piston stopper is retained in said position during evacuation and filling.

2. Method according to claim 1, wherein filling takes place with atmospheric overpressure, particularly a slight overpressure.

3. Method according to claim 1, wherein the disappearance of the vacuum is used for determining the filling status.

4. Method according to claim 2, wherein an overpressure still present in the filled state of the injector (35) is reduced by a bypass in the liquid supply line.

5. Method according to claim 1, wherein the discharge opening of the injector (35) is closed after filling.

6. Device for filling needle-free injectors 35), said device comprising:
    a mounting support for at least one of the injectors (35),
    a vacuum bell jar (1) having an interior space that is adapted to be connected to the interior of the injector (35),
    a filling needle (4), which is adapted to be connected to a discharge opening of the injector (35),
    a closing device for the filling needle (4),
    a connection (16) for a liquid to be filled and a vacuum connection (2).

7. Device according to claim 6, wherein the mounting support for the injector (35) has a stop (45) for the piston stopper (38).

8. Device according to claim 6, wherein the bell jar (1) is displacedly retained and spring-loaded on the filling needle (4) facing the latter.

9. Device according to claim 6, wherein the closing device has a closing rod axially traversing the filling needle (4) and provided with a drive (6).

10. Device according to claim 6, wherein the bell jar (1) has a suction opening (32) surrounding the filling needle (4).

11. Device according to claim 6, wherein the filling needle is equipped with a sealing system for providing a seal between the needle tip and the injector.

* * * * *

UNITED STATES PATENT AND TRADEMARK OFFICE
CERTIFICATE OF CORRECTION

PATENT NO. : 6,640,842 B1
DATED : November 4, 2003
INVENTOR(S) : Bernd Laukenmann et al.

It is certified that error appears in the above-identified patent and that said Letters Patent is hereby corrected as shown below:

Column 1,
Line 21, "to A fill" should be -- to fill --.

Signed and Sealed this

Sixth Day of July, 2004

JON W. DUDAS
*Acting Director of the United States Patent and Trademark Office*